United States Patent
Ricca et al.

(10) Patent No.: US 6,503,982 B2
(45) Date of Patent: Jan. 7, 2003

(54) PROCESS FOR GELLING AQUEOUS MEDIA, USE OF COPOLYESTERS AS GELLING AGENTS FOR AQUEOUS MEDIA AND NEW GELLING COPOLYESTERS FOR AQUEOUS MEDIA

(75) Inventors: Jean-Marc Ricca, Paris; Etienne Fleury, Irigny, both of (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/947,456

(22) Filed: Sep. 6, 2001

(65) Prior Publication Data

US 2002/0032301 A1 Mar. 14, 2002

Related U.S. Application Data

(63) Continuation of application No. 09/038,214, filed on Mar. 11, 1998.

(51) Int. Cl.$^7$ .............................. C08J 2/32; C08G 63/02
(52) U.S. Cl. ...................... 524/801; 528/274; 528/295; 528/298; 528/308; 528/308.6; 524/601; 524/604; 524/605; 524/609; 524/810

(58) Field of Search ................................. 528/274, 295, 528/298, 308, 308.6; 524/601, 604, 605, 609, 800, 801

(56) References Cited

U.S. PATENT DOCUMENTS

| 4,300,580 A | 11/1981 | O'Neill | 132/7 |
| 5,369,210 A | 11/1994 | George | 528/293 |

FOREIGN PATENT DOCUMENTS

| WO | WO 96/03964 | 2/1996 |

OTHER PUBLICATIONS

Copy of International Search Report.

*Primary Examiner*—Samuel A. Acquah

(57) ABSTRACT

Process of gelification of aqueous medium with a copolyester oligomer comprising essentially oxyalkylenated or ocycycloalkylenated or polyoxyalkylenated dicarboxylate units at least 35 mole % of said units being similar units of which the correspondent homolymer is crystalline, at least 7 mole % of said units being bearing units of hydrophobic(s) sulfonated functions, the molecular mass in weight of said copolyesters oligomer being less than 20,000. For example: the terephtalic polyoxyethylenated sulfonated oligomers of high content of polyethyleneterephtalate.

17 Claims, No Drawings

PROCESS FOR GELLING AQUEOUS MEDIA, USE OF COPOLYESTERS AS GELLING AGENTS FOR AQUEOUS MEDIA AND NEW GELLING COPOLYESTERS FOR AQUEOUS MEDIA

This application is a continuation application of application Ser. No. 09/038,214 filed on Mar. 11, 1998.

The subject of the present invention is a process for gelling aqueous media with the aid of copolyester oligomers, the use of copolyester oligomers as gelling agents for aqueous media and of new gelling copolyester oligomers for aqueous media.

A first subject of the invention relates to a process for gelling aqueous media by introducing into the said media an effective quantity of at least one water-soluble or water-dispersible copolyester oligomer comprising essentially dicarboxylate units of formula (I)

[—CO—A—CO—O—X—O]  (I)

in which formula

A represents an aromatic or aliphatic divalent hydrocarbon group,

X represents a divalent alkylene, cycloalkylene or polyoxyalkylene group, at least 35 mol %, preferably at least 40 mol %, most particularly from 40 to 70 mol % of the said units of formula (I) being similar units whose corresponding homopolymer is crystalline, at least 7 mol %, preferably at least 10 mol %, most particularly 10 to 25 mol % of the said units of formula (I) being units in which the group A is a carrier of hydrophilic functional group(s).

Among the groups A of the units of formula (I), there may be mentioned:

the $C_6$–$C_{14}$ mono- or polyarylene groups, the $C_1$–$C_9$ alkylene groups, not carrying a hydrophilic functional group, such as the 1,4-phenylene, 1,3-phenylene, 1,6-naphthalene, 1,6-cyclohexylene, ethylene, trimethylene, tetramethylene or hexamethylene groups;

the $C_6$–$C_{14}$ mono- or polyarylene groups, or $C_1$–$C_9$ alkylene groups, carrying hydrophilic, preferably anionic, functional group(s), in particular sulphonates of alkali metals, most particularly sodium, or sulphonates of mono-, di-, tri- or tetraalkylammonium in which the alkyl radical is a $C_1$–$C_{20}$ radical, such as sulpho-1,4-phenylene, sulpho-1,3-phenylene, sulpho-1,2-phenylene, sulphonaphthalene, sulphobiphenylene or sulphoethylene groups.

Among the groups X of the units of formula (I), there may be mentioned the $C_2$–$C_{10}$ alkylene groups, such as polymethylenes (—$CH_2$—)$_x$ with x ranging from 2 to 10, 2,2-dimethylpropanediyl, 1,6-cyclohexylene, polyoxyalkylene groups of formula (—Y—O)$_y$Y—, Y representing a $C_2$–$C_4$ alkylene, in particular ethylene, group, y ranging from 1 to 5.

Among the units of formula (I) in which the corresponding homopolymer is crystalline, there may be mentioned in particular those in which the corresponding homopolymers are polyterephthalates, polyisophthalates, polynaphthates, polyhexahydro-terephthalates, polysebacates, polyadipates and polyazelates of ethylene glycol, dioxyethylene glycol, tetramethylene glycol, hexamethylene glycol, octamethylene glycol, decamethylene glycol, 2,2-dimethy-1,3-propanediol or 1,6-cyclohexanediol.

Preferably, the said units of formula (I) are chosen from those whose corresponding homopolymer has a melting point greater than the desired temperature for obtaining the gelling of the aqueous medium to be gelled, this desired gelling temperature being most generally close to room temperature, that is to say of the order of 10 to 40° C.

Thus, there may be mentioned most particularly the units of formula (I) whose corresponding homopolymer is one of the following homopolymers, whose melting temperature is given in particular in "Properties of polymers" by D. W. VAN KREVELEN (Elsevier Publishing Company 1972):

polyethylene terephthalate, of melting point tc=284° C.

polydecamethylene terephthalate, of melting point tc=138° C.

polyethylene adipate, of melting point tc=65° C.

polydecamethylene adipate, of melting point tc=85° C.

The chain ends of the copolyester oligomers used for carrying out the process of the invention may be similar or different and chosen from the groups of formulae —A—CO—O—(X—O)$_n$—H  (II$_1$)

the said groups (II$_1$) being optionally at least partially sulphated or phosphated, —A—CO—O—(X—O)$_{\bar{n}}$—Z  (II$_2$)

—A—CO—Z'  (II$_3$)

—A—CO—O—(X'—O)$_{\bar{p}}$—Z"  (II$_4$)

in which formulae

A, X and n have the meaning given above,

Z represents a $C_2$–$C_{31}$ alkyloyl or aryloyl group optionally carrying an anionic, preferably sulphonate, functional group such as sulphobenzoyl $MO_3SC_6H_4C(O)$— where M is an alkali metal Z' represents a polyalkoxysulphonate group, in particular of formula $(MO_3S)(CH_2)_q(CH_2—CH_2—O)(RO)_r$—, where M is an alkali metal, q is equal to 0 or 1, R is an ethylene or propylene group, r ranges from 0 to 2

X' represents a $C_2$–$C_8$ alkylene group, Z" represents a $C_1$–$C_{30}$ alkyl or aryl group and p ranges from 0 to 6.

Other units may, in addition, be present at the chain ends and in minor quantities, such as groups of formula

—A—CO—OH  (II5)

where A has the meaning given above.

Preferably, the weight-average molecular mass of the said copolyester oligomers is less than 20,000, preferably less than 15,000, most particularly from 5000 to 10,000.

The weight-average molecular masses are measured by gel permeation chromatography, in dimethylacetamide containing $10^{-2}$ N LiBr, at 100° C. The results are expressed as polystyrene equivalents.

The said copolyester oligomers can be obtained by the customary processes for preparing polyesters by the molten route, the solvent route or the interfacial route, which processes involve the following reactions:

esterification of diacids and of diols and polycondensation transesterification of diesters and of diols and polycondensation autocondensation of hydroxy acids Schotten-Baumann reaction using diols and acid chlorides and polycondensation polymerization of lactones by controlling the minimum content of similar units (I) by the initial stoichiometric ratios of the various monomers and by controlling side reactions.

A particularly advantageous mode of preparation is that by transesterification/polycondensation and/or esterification/polycondensation by the molten route with the aid of a transesterification and/or esterification catalyst.

Control of the structure is obtained by controlling the minimum content of similar units (I) by the initial stoichiometric ratios of the different diacid and/or diester and diol monomers and by using an etherification-limiting agent, which limiting agent may be a basic compound such as aliphatic or aromatic amines or a hydroxide or acetate of alkali or alkaline-earth metals.

Control of the molecular mass is obtained in a manner known to persons skilled in the art, by a suitable compromise between pressure, temperature and time, and/or by introducing a monofunctional monomer.

The production of chain ends of formula of the $(II_2)$, $(II_3)$ and $(II_4)$ type can be achieved using monoacid monomers for the chain ends of formula $(II_2)$, a hydroxypolyalkoxyalkylsulphonate for the chain ends of formula $(II_3)$, a polyalkylene glycol monoether or a monoalcohol for the chain ends of formula $(II_4)$.

Terminal groups of formula $(I_1)$ which are at least partially sulphated or phosphated can be obtained, if desired, by treating the copolyester oligomer prepared, with the aid of sulphuric, sulphamic or phosphoric acid.

One type of water-soluble or water-dispersible copolyester oligomer particularly well suited to the process of the invention consists in water-soluble or water-dispersible copolyester oligomers having dicarboxylate repeating units of formula (I), at least 35 mol %, preferably 40 mol %, most particularly from 40 to 70 mol % of the said units of formula (I) being similar units whose group A represents a 1,4-phenylene, 1,3-phenylene, 1,6-naphthalene, 1,6-cyclohexylene, ethylene, trimethylene, tetramethylene or hexamethylene group and the group X represents a $C_2$–$C_1$ alkylene group, preferably ethylene, tetramethylene, hexamethylene, octamethylene, decamethylene or ethylene oxyethylene and whose corresponding homopolymer is crystalline.

Among the copolyester oligomers which are particularly suitable for carrying out the invention, there may be mentioned the water-soluble or water-dispersible copolyester oligomers comprising essentially dicarboxylate units of formula (I')

[—CO—A'—CO—O—(CH$_2$—CH$_2$—O)$_{n'}$—] (I')

in which formula

A' represents a 1,4-phenylene, 1,3-phenylene, 1,6-naphthalene, 1,6-cyclohexylene, ethylene, trimethylene, tetramethylene, hexamethylene or sulpho-1,3-phenylene group n' ranges from 1 to 4, at least 35 mol %, preferably at least 40 mol %, most particularly from 40 to 70 mol % of the said units of formula (I') being similar units of formula

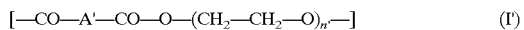

where A'' represents a 1,4-phenylene, 1,3-phenylene, 1,6-naphthalene, 1,6-cyclohexylene, ethylene, trimethylene, tetramethylene or hexamethylene group at least 7 mol %, preferably at least 10 mol %, most particularly from 10 to 25 mol % of the said units of formula (I') being units in which the A' group is a sulpho-1,3-phenylene group.

Preferably, the weight-average molecular mass of the said copolyester oligomers is less than 20,000, preferably less than 15,000, most particularly from 5000 to 10,000.

The chain ends of the said oligomers may be similar or different and represented by the groups of formulae

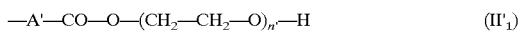 (II'$_1$)

the said groups (II'$_1$) being optionally at least partially sulphated or phosphated,

 (II'$_2$)

—A'—CO—Z' (II'$_3$)

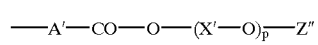 (II'$_4$)

in which formulae

A', X and n' have the meaning given above,

Z represents a $C_2$–$C_{31}$ alkyloyl or aryloyl group optionally carrying an anionic, preferably sulphonate, functional group such as sulphobenzoyl MO$_3$SC$_6$H$_4$C(O)— where M is an alkali metal Z' represents a polyalkoxysulphonate group of formula (MO$_3$S)(CH$_2$)$_q$(CH$_2$—CH$_2$—O)(RO)$_r$—, where M is an alkali metal, q is equal to 0 or 1, R is an ethylene or propylene group, r ranges from 0 to 2

X' represents a $C_2$–$C_8$ alkylene group, Z'' represents a $C_1$–$C_{30}$ alkyl or aryl group and p ranges from 0 to 6.

The preferred chain ends are those of formula (II'$_1$).

The said oligomers may also have at the chain ends, and in minor quantities, groups of formula

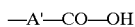

in which formula A' has the meaning given above.

Among the most preferred copolyester oligomers, there may be mentioned the water-soluble or water-dispersible terephthalic copolyester oligomers comprising essentially dicarboxylate units of formula (I'$^1$)

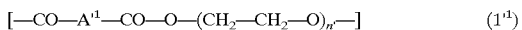 (1'$^1$)

in which formula

A'$^1$ represents a 1,4-phenylene, sulpho-1,3-phenylene and, optionally, 1,3-phenylene group n' ranges from 1 to 4;

at least 35 mol %, preferably at least 40 mol %, most particularly from 40 to 70 mol % of the said units of formula (I'$^1$) being similar units of formula

 (I''$^1$)

where A'''$^1$ represents a 1,4-phenylene group;

at least 7 mol %, preferably at least 10 mol %, most particularly from 10 to 25 mol % of the said units of formula (I'$^1$) being units in which the A'$^1$ group is a sulpho-1,3-phenylene group;

optionally up to 20 mol %, preferably up to 5 mol % of the said units of formula (I'$^1$) being units in which the A'$^1$ group is a 1,3-phenylene group, the weight-average molecular mass of the said copolyester oligomers being less than 20,000, preferably less than 15,000, most particularly from 5000 to 10,000.

The chain ends of the said oligomers may be similar or different and represented by the groups of formulae

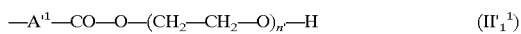 (II'$_1^1$)

the said groups (II'$_1^1$) being optionally at least partially sulphated or phosphated,

 (II'$_2^1$)

 (II'$_3^1$)

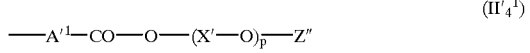 (II'$_4^1$)

in which formulae

A'$^1$, X and n' have the definition given above,

Z represents a $C_2$–$C_{31}$ alkyloyl or aryloyl group optionally carrying an anionic, preferably sulphonate, functional group such as sulphobenzoyl $MO_3SC_6H_4C(O)$— where M is an alkali metal Z' represents a polyalkoxysulphonate group of formula $(MO_3S)(CH_2)_q(CH_2-CH_2-O)(RO)_r$—, where M is an alkali metal, m is equal to 0 or 1, R is an ethylene or propylene group, r ranges from 0 to 2

X' represents a $C_2$–$C_8$ alkylene group, Z" represents a $C_1$–$C_{30}$ alkyl or aryl group and p ranges from 0 to 6.

The preferred chain ends are those of formula (II'$_1^1$).

The said oligomers may also have at the chain ends, and in minor quantities, groups of formula

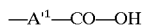

in which formula A'$^1$ has the definition given above.

Among the aqueous media which can be gelled according to the process of the invention, there may be mentioned, water, mixtures of water/solvent(s) compatible with water such as ethanol, isopropanol, ethylene glycol, propylene glycol, hexylene gylcol, glycerol or sorbitol. The quantity of solvent may represent up to 60% by weight of the said mixture.

The said aqueous medium to be gelled may also consist of a simple or multiple "water-in-oil" or "oil-in-water" emulsion; the said aqueous medium will be termed "vehicle". The said aqueous medium to be gelled may be present as such or in various compositions, for example plant-protection and pharmaceutical compositions, and most particularly in cosmetic compositions.

The term cosmetic composition or formulation is understood to mean all the cosmetic products or preparations of the types described in Annex I ("Illustrative list by category of cosmetic products") of the European Directive No. 76/768/EEC of Jul. 27, 1976, called cosmetic directive.

The cosmetic compositions can be formulated to a large number of product types for the skin and/or the hair, such as foams, gels (hair-styling gels in particular), conditioners, formulations for hair styling or for facilitating hair combing, rinsing formulas, hand and body lotions, skin moisturizing regulators, toilet milks, make-up removing compositions, creams or lotions for protecting against sunlight and ultraviolet radiation, care creams, anti-acne preparations, local analgesics, mascaras, products intended to be applied to the lips or other mucous membranes, and many other compositions of the same type.

These cosmetic compositions require a vehicle, or a mixture of several vehicles, which is present in the said compositions at concentrations of between about 0.5% and 99.5%, generally between about 5 and 90%.

The choice of appropriate vehicle depends on the nature of the ingredients and on the destination of the said compositions, depending on whether the formulated product is intended to be left on the surface where it has been applied (for example sprays, foams, tonic lotion or gels) or on the contrary rinsed after use (for example shampoo, conditioner, rinsing lotions).

The aqueous vehicles present in the cosmetic compositions may contain, in addition, $C_1$–$C_6$ alcohols, in particular methanol, ethanol or isopropanol.

They may also contain another solvent which makes it possible to solubilize or disperse, in the aqueous medium, the various ingredients used in the said compositions.

The said vehicles may thus contain, in addition, a wide variety of other solvents such as acetone, hydrocarbons, halogenated hydrocarbons, linalol, esters and volatile silicones. The various solvents which can be used in the aqueous vehicles may be miscible or immiscible with each other.

When the cosmetic compositions are provided in the form of sprays, tonic lotions, gels or foams, the preferred vehicles comprise, in addition to water, ethanol, volatile derivatives of silicone, and mixtures thereof.

The formulations for aerosol sprays and foams may also contain a propellant capable of generating the products in the form of uniform, fine sprays or foam. By way of examples, there may be mentioned trichlorofluoromethane, dichlorodifluoromethane, difluoroethane, dimethyl ether, propane, n-butane or isobutane.

The said aqueous vehicles may take a large number of forms, in particular those of emulsions, including water-in-oil and oil-in-water emulsions, and multiple emulsions, in which the desired viscosity may be as high as 2,000,000 mPa·s.

In addition to the aqueous vehicle, the cosmetic compositions may contain surfactants used to disperse, emulsify, solubilize and stabilize various compounds used in particular for their emollient or humectant properties. They may be of the anionic, non-ionic, cationic, zwitterionic or amphoteric type; there may be mentioned by way of examples
anionic surfactants such as
  alkyl ester sulphonates
  alkyl sulphates
  alkyl amide sulphates
  salts of saturated or unsaturated fatty acids
non-ionic surfactants such as
  polyoxyalkylenated alkylphenols
  glucose amides, glucamides;
  glycerol amides derived from N-alkylamines
  polyoxyalkylenated $C_8$–$C_{22}$ aliphatic alcohols
  products resulting from the condensation of ethylene oxide with a hydrophobic compound resulting from the condensation of propylene oxide with propylene glycol,
  amine oxides
  alkyl polyglycosides and their polyoxyalkylenated derivatives
  $C_8$–$C_{20}$ fatty acid amides
  ethoxylated fatty acids
  ethoxylated amidoamines, amines or amides
amphoteric or zwitterionic surfactants such as those of the betaine type such as betaines sulphobetaines amidoalkylbetaines and sulphobetaines alkylsultaines the products of condensation of fatty acids and protein hydrolysates, cocoamphoacetates and cocoamphodiacetates alkylampho-propionates or dipropionates, amphoteric derivatives of alkylpolyamines Conditioners may also be present.

Among them, there may be mentioned those of animal origin, those of synthetic origin which are more widely known under the name polyquaternium such as 2-, 7- and 10-polyquaterniums, cationic derivatives of polysaccharides, such as hydroxyethyl cocodimonium cellulose, guar hydroxypropyl trimonium chloride, hydroxypropyl guar hydroxypropyl trimonium chloride, non-volatile derivatives of silicones such as amodimethicone, cyclomethicones, non-water-soluble and non-volatile organopolysiloxanes such as oils, resins or gums such as diphenylmethicone gums.

The cosmetic compositions may also contain polymers having film-forming properties which can be used to provide a fixing function. These polymers are generally present at concentrations of between 0.01 and 10%, preferably between 0.5 and 5%. They are preferably of the type comprising polyvinylpyrrolidone, polyvinylpyrrolidone/ methyl methacrylate copolymers, polyvinylpyrrolidone/ vinyl acetate copolymers, ethylene glycol polyterephthalate/ polyethylene glycol copolymers, and sulphonated terephthalic copolyester polymers.

The cosmetic compositions may also contain polymeric derivatives exerting a protective function, in quantities of the order of 0.01–10%, preferably about 0.1–5% by weight, derivatives such as cellulosic derivatives polyvinyl esters grafted on polyalkylene backbones polyvinyl alcohols sulphonated terephthalic copolyester polymers ethoxylated monoamines or polyamines, polymers of ethoxylated amines.

The performance of the cosmetic compositions can also be improved by the use of plasticizing agents, in a quantity which may range from 0.1 to 20% of the formulation, preferably from 1 to 15%. Among these agents, there may be mentioned adipates, phthalates, isophthalates, azelates, stearates, copolyol silicones, glycols, castor oil, or mixtures thereof.

Advantageously, it is also possible to add to these compositions metal-sequestering agents, more particularly those sequestering calcium such as citrate ions, or polymeric dispersing agents in a quantity of the order of 0.1–7% by weight, in order to control the calcium and magnesium hardness, agents such as water-soluble salts of polycarboxylic acids polyethylene glycols having a molecular mass of the order of 1000 to 50,000.

It is also possible to incorporate into the cosmetic compositions humectant agents; there may be mentioned glycerol, sorbitol, urea, collagen, gelatin, and emollients which are generally chosen from alkylmonoglycerides, alkyldiglycerides, triglycerides such as the oils extracted from plants and vegetables or oils of animal origin or their hydrogenated derivatives, mineral oils or paraffin oils, diols, fatty esters, silicones.

It is possible to add to these compounds, in combination, inorganic particles or powders such as calcium carbonate, inorganic oxides in powdered form or in colloidal form such as titanium dioxide, silica, aluminium salts, kaolin, talc, clays and derivatives thereof.

One or more perfumes, colorants and/or opacifying agents such as pigments are generally added to these ingredients.

To protect the skin and/or hair from damage caused by sunlight and UV rays, it is possible to add to these formulations sunscreens which are either chemical compounds strongly absorbing UV radiation or inorganic particles such as zinc oxide, titanium dioxide or cerium oxides.

Preservatives such as p-hydroxybenzoic acid esters, sodium benzoate or any chemical agent avoiding the proliferation of bacteria or of moulds and which is traditionally used in cosmetic compositions are generally introduced into these compositions in an amount of 0.01 to 3% by weight.

Agents modifying water activity and substantially increasing osmotic pressure, such as carbohydrates or salts, can sometimes be used.

The cosmetic composition may also contain viscosity-promoting or gelling polymers, such as cross-linked polyacrylates, hydrocolloids obtained by fermentation such as xanthan gum and Rheozan, cellulose derivatives such as hydroxypropylcellulose, carboxymethylcellulose, guars and derivatives thereof, and the like, used alone or in combination.

The quantity of water-soluble or water-dispersible copolyester oligomer which can be used for carrying out the process of the invention depends on the said oligomer and on the aqueous medium to be gelled; it generally represents at least 0.5%, preferably at least about 2%, more preferably at least about 5%, more particularly of the order of 8 to 40%, and most particularly from 10 to 30% of the weight of the gelled aqueous medium.

The introduction of the said oligomers into the aqueous medium to be gelled can be carried out by conventional techniques known to persons skilled in the art. This can be carried out at low temperature or preferably at high temperature, the oligomers being introduced, under low shearing, into the aqueous medium previously heated to a temperature of between about 60 and 85° C.

A second subject of the invention consists in the use of the copolyester oligomers described above comprising essentially the units of formula (I), (I') or (I'¹), at least 35 mol %, preferably at least 40 mol %, most particularly 40 to 70 mol % of the said units of formula (I), (I') or (I'¹) being similar units whose corresponding homopolymer is crystalline, as aqueous media-gelling agents.

The nature of the aqueous media as well as the quantities of the said oligomers which can be used have already been mentioned above.

Another subject of the invention consists, as new products, of copolyester oligomers comprising essentially dicarboxylate units of formula (I')

$$[-CO-A'-CO-O-(CH_2-CH_2-O)_{n'}-]\qquad (I')$$

in which formula

A' represents a 1,4-phenylene, 1,3-phenylene, 1,6-naphthalene, 1,6-cyclohexylene, ethylene, trimethylene, tetramethylene, hexamethylene or sulpho-1,3-phenylene group n' ranges from 1 to 4, at least 35 mol %, preferably at least 40 mol %, most particularly from 40 to 70 mol % of the said units of formula (I') being similar units of formula

[—CO—A"—CO—O—CH$_2$—CH$_2$—O—]  (I")

where A" represents a 1,4-phenylene, 1,3-phenylene, 1,6-naphthalene, 1,6-cyclohexylene, ethylene, trimethylene, tetramethylene or hexamethylene group, at least 7 mol %, preferably at least 10 mol %, most particularly from 10 to 25 mol % of the said units of formula (I') being units in which the A' group is a sulpho-1,3-phenylene group;

the chain ends of the said copolyester oligomers being similar or different and represented by the terminal groups of formula —A'—CO—O—(CH$_2$—CH$_2$—O)$_{n'}$—H optionally at least partially sulphated or phosphated, in which formula A' has the meaning given above, n' ranges from 1 to 4.

Preferably, the weight-average molecular mass of the said copolyester oligomers is less than 20,000, preferably less than 15,000, most particularly from 5000 to 10,000.

The said oligomers can also have at the chain ends, and in minor quantities, groups of formula

—A'—CO—OH in which formula A' has the meaning given above.

Preferred copolyester oligomers are terephthalic copolyester oligomers comprising essentially dicarboxylate units of formula (I'$^1$)

[—CO—A'$^1$—CO—O—(CH$_2$—CH$_2$—O)$_{n'}$—]  (I'$^1$)

in which formula

A'$^1$ represents a 1,4-phenylene, sulpho-1,3-phenylene and, optionally, 1,3-phenylene group and n' ranges from 1 to 4;

at least 35 mol %, preferably at least 40 mol %, most particularly from 40 to 70 mol % of the said units of formula (I'$^1$) being similar units of formula

[—CO—A"$^1$—CO—O—CH$_2$—CH$_2$—O—]  (I"$^1$)

where A"$^1$ represents a 1,4-phenylene group;

at least 7 mol %, preferably at least 10 mol %, most particularly from 10 to 25 mol % of the said units of formula (I'$^1$) being units in which the A'$^1$ group is a sulpho-1,3-phenylene group;

optionally up to 20 mol %, preferably up to 5 mol % of the said units of formula (I'$^1$) being units in which the group A'$^1$ is a 1,3-phenylene group;

the chain ends of the said copolyester oligomers being similar or different and represented by the terminal groups of formula —A'$^1$—CO—O—(CH$_2$—CH$_2$—O)$_{n'}$—H optionally at least partially sulphated or phosphated, in which formula A'$^1$ has the meaning given above, n' ranges from 1 to 4;

the weight-average molecular mass of the said copolyester oligomers being less than 20,000, preferably less than 15,000, most particularly from 5000 to 10,000.

The said oligomers can also have at the chain ends, and in minor quantities, groups of formula

—A'$^1$—CO—OH in which formula A'$^1$ has the meaning given above.

The new terephthalic copolyester oligomers which form the subject of the invention can be prepared by esterification and/or transesterification/poly-condensation of a monomer composition based:

on terephthalic (Tp) acid, anhydride or diester on sulphoisophthalic (SIp) acid, anhydride or diester optionally on isophthalic (Ip) acid, anhydride or diester, and on ethylene glycol (EG)

in relative amounts corresponding to an (SIp)/[(Tp)+(SIp)+(Ip)] molar ratio of at least 7/100, preferably of at least 10/100, most particularly of from 10/100 to 25/100 an (Ip)/[(Tp)+(SIp)+(Ip)] molar ratio of not more than 20/100, preferably of not more than 5/100 an (EG)/[(Tp)+(SIp)+(Ip)] molar ratio of from 2/1 to 3/1 in the presence of an esterification and/or transesterification catalyst and an etherification-limiting agent.

The terephthalic (Tp) monomer is preferably used in the form of a lower diester (di(C$_1$–C$_4$)alkyl diester), preferably the dimethyl diester.

The sulphoisophthalic (SIp) monomer is preferably used in the form of an alkali metal sulphonate (in particular sodium sulphonate) of a lower (C$_1$–C$_4$ alkyl), preferably methyl, diester. Sodium dimethyl 5-oxysulphonylisophthalate may be mentioned most particularly.

The optional isophthalic (Ip) monomer is preferably used in the form of isophthalic acid.

When all of the "diacid" monomers are used in the form of diesters, the transesterification (exchange) operation between these "diacid" monomers and ethylene glycol is carried out at a temperature above or equal to 130° C., preferably of about 140 to 220° C. and most particularly of about 180 to 220° C.; at this temperature the methanol (in the preferred case of the methyl diesters) formed is preferably removed from the reaction medium by distillation.

This exchange operation is carried out in the presence of a metallic transesterification catalyst and an etherification-limiting agent.

The said catalyst is preferably a metal carboxylate, such as manganese acetate, zinc acetate, cobalt acetate or calcium acetate, or an organic or inorganic titanate such as butyl titanate, nitrilo-2,2',2"-triethyl titanate (or titanium aminotriethanolate which also acts as etherification-limiting agent) or calcium titanate.

The preferred catalysts are the organic titanates; they are used in amounts of at least about 0.001% by weight, expressed as titanium, preferably from about 0.002% to 0.02% by weight of titanium relative to the weight of reactants present.

The etherification-limiting agent can be a basic compound such as aliphatic or aromatic amines (triethanolamine, guanidine carbonate, dimethylaniline, naphthylamine, etc.) or an alkali-metal or alkaline-earth metal hydroxide or acetate (sodium or potassium acetate, sodium benzoate, etc.). It is generally used in an amount from about 0.001% to 0.05% relative to the weight of reactants present.

The duration of the exchange operation is from 1 to 4 hours; it is generally from about 2 to 3 hours.

When more than 90% of the theoretical amount of methanol has been distilled off, the excess polyol is removed by bringing the temperature of the reaction medium to 230° C.

The polycondensation operation is preferably carried out at a temperature of about 230 to 280° C., preferably of about 240 to 260° C., in another reactor brought beforehand to this temperature and gradually placed under vacuum down to a pressure which may be as low as 10 Pa; a pressure reduction down to about 10 millibar lasts for about 40 minutes.

The polycondensation operation takes place with removal of polyol molecules, this operation being stopped when the motor torque of the stirrer shaft indicates a value equivalent to about 0.5 to 5 newton.meters for a temperature of 250° C. of the reaction mass and a stirring speed of 80 revolutions/ minute of an anchor-shaped spindle in a 7.5 liter reactor. The vacuum is then broken with nitrogen and the polymer is poured into a mould; after cooling, the polymer is ground.

When one of the "diacid" monomers is present in the form of diacid or anhydride and the other(s) is(are) in the form of diester(s), the said copolyester oligomers are obtained by first carrying put a transesterification operation of the diester monomers with ethylene glycol under the conditions described above, followed by an esterification operation in the medium of the diacid or anhydride monomer with ethylene glycol, and then polycondensation under the conditions described above, the total amount of ethylene glycol being divided between the two operations (transesterification and esterification).

If necessary, the esterification operation is carried out by adding, to the reaction medium resulting from the transesterification operation, monomer in diacid or anhydride form and ethylene glycol placed in suspension beforehand, at a temperature corresponding to that at the end of the exchange; the introduction period is about 1 hour.

This esterification operation is carried out at a temperature of about 230 to 280° C., preferably of about 250 to 260° C., in the presence of a catalyst of the same type as the transesterification catalyst, and an etherification-limiting agent.

The operation is carried out in the presence of the same types of catalyst and of etherification-limiting agent as those used in the transesterification operation, and in the same proportions.

The reaction is carried out with removal of water, which is removed from the reactor at the same time as the excess polyol.

The following examples are given by way of illustration.

EXAMPLE 1

The following reagents are introduced into a 7.5 liter stainless-steel reactor fitted with an anchor-shaped stirrer rotating at 80 rev/min, a jacket for circulating a heat-exchange liquid, and a distillation column controlled by an electrovalve:

11.47 mol of dimethyl terephthalate 2.53 mol of dimethyl 5-(sodium sulphonate)isophthalate 39.16 mol of ethylene glycol 54 ppm by weight of titanium, in the form of titanium aminotriethanolate as catalyst and etherification-limiting agent.

The mixture is preheated to 180° C. It is then brought to a temperature of 220° C. over about 130 minutes, in order to distil off more than 90% of the theoretical amount of methanol.

The reaction mixture is then brought to 230° C. over 30 minutes. When the reaction mass has reached this temperature, a suspension having the composition below is introduced over 60 minutes, still at 230° C.:

0.5 mol of isophthalic acid 2.36 mol of terephthalic acid 8 mol of ethylene glycol The reaction mass is then brought to a temperature of 250° C. over 60 minutes.

During the period of introduction of the mixture and during the period of heating up to 250° C., a mixture of water and ethylene glycol is distilled off without retrogradation.

The reaction mixture is then transferred into an autoclave preheated to 250° C. and is then placed under a reduced pressure of 100 millibar over 22 minutes. After 2 minutes under these temperature and pressure conditions, the reaction mass is cast and cooled.

The copolyester obtained has the structural characteristics described in Table 1.

EXAMPLE 2

The operations described in Example 1 are repeated starting with the same quantities of reagents and under the same operating conditions up to the step of transferring into an autoclave preheated to 250° C.

The reaction mixture is then transferred into an autoclave preheated to 250° C. and then placed under a reduced pressure of 100 millibar over 22 minutes. After 45 minutes (instead of 2 minutes in Example 1) under these temperature and pressure conditions, the reaction mass is cast and cooled.

The copolyester obtained has the structural characteristics described in Table 1.

EXAMPLE 3

The operations described in Example 1 are repeated starting with the same quantities of reagents and under the same operating conditions up to the step of transferring into an autoclave preheated to 250° C.

The reaction mixture is then transferred into an autoclave preheated to 250° C. and then placed under a reduced pressure of 200 millibar (instead of 100 millibar) over 15 minutes. After 2 minutes under these temperature and pressure conditions, the reaction mass is cast and cooled.

The copolyester obtained has the structural characteristics described in Table 1.

Comparative Example 4

The steps described in Example 1 are repeated, under the same operating conditions, using:

11.47 mol of dimethyl terephthalate 2.53 mol of dimethyl 5-(sodium sulphonate)isophthalate 39.16 mol of ethylene glycol 54 ppm by weight of titanium, in the form of butyl-orthotitanate, as sole catalyst, followed by the introduction, at 230° C., of a suspension of 2.87 mol of isophthalic acid 8 mol of ethylene glycol The copolyester obtained has the structural characteristics described in Table 1.

EXAMPLE 5

The steps described in Example 1 are repeated, under the same operating conditions, using:

11.47 mol of dimethyl terephthalate
2.53 mol of dimethyl 5-(sodium sulphonate)isophthalate
39.16 mol of ethylene glycol
54 ppm by weight of titanium, in the form of titanium aminotriethanolate as catalyst and etherification-limiting agent,
followed by the introduction, at 230° C., of a suspension of
2.87 mol of isophthalic acid
8 mol of ethylene glycol The copolyester obtained has the structural characteristics described in Table 1.

Comparative Example 6

The following reagents are introduced into a stainless-steel reactor identical to that described in Example 1:
15.16 mol of dimethyl terephthalate
1.99 mol of dimethyl 5-(sodium sulphonate)isophthalate
48 mol of ethylene glycol
54 ppm by weight of titanium, in the form of butyl orthotitanate as catalyst and etherification-limiting agent.

The mixture is preheated to 180° C. It is then brought to a temperature of 220° C. over about 130 minutes, in order to distil off more than 90% of the theoretical amount of methanol.

The reaction mixture is then brought to 250° C. over 90 minutes. When the reaction mass has reached this temperature, the reaction mixture is transferred into an autoclave preheated to 250° C. and is then placed under a reduced pressure of 1 millibar over 60 minutes. The reaction mixture is then maintained under these temperature and pressure conditions for 90 minutes, after which the reaction mass is cast and cooled.

The copolyester obtained has the structural characteristics described in Table 1.

Comparative Example 7

The steps described in Example 5 are repeated, under the same operating conditions, using:
15.16 mol of dimethyl terephthalate
1.99 mol of dimethyl 5-(sodium sulphonate)isophthalate
48 mol of ethylene glycol
54 ppm by weight of titanium, in the form of titanium aminotriethanolate as catalyst and etherification-limiting agent.

The copolyester obtained has the structural characteristics described in Table 1.

EXAMPLE 8

The steps described in Example 1 are repeated, under the same operating conditions, using:
11.47 mol of dimethyl naphthalate
2.53 mol of dimethyl 5-(sodium sulphonate) isophthalate
39.16 mol of ethylene glycol
54 ppm by weight of titanium, in the form of titanium aminotriethanolate as catalyst and etherification-limiting agent,
followed by the introduction, at 230° C., of a suspension of
0.5 mol of isophthalic acid
2.36 mol of naphthalinedicarboxylic acid
8 mol of ethylene glycol The copolyester obtained has the structural characteristics described in Table 1.

The copolyester oligomers or polymers prepared in Examples 1–8 are tested for their property as aqueous media-gelling agent, by dissolving in water at 70° C. and mixing for 1 hour. 2×7 water/copolyester mixtures were thus prepared, containing 10% or 20% by weight of the said copolyesters.

The state of the mixtures obtained (gel or liquid) is given in Table 1.

In this table:

"mol % of diacid units" corresponds to the content, in %, of each diacid or diester used relative to the total amount of diacids or diesters used.

"Tp" means: terephthalic unit (Examples 1 to 7)

"Np" means: naphthalic unit (Example 8)

"Ip" means: isophthalic unit

"SIp" means: sulphoisophthalic unit

The characteristics of the "glycol" part of the copolyesters are obtained by methanolysis of the products at 190° C. for 16 hours, followed by analysis by the gas chromatography technique and assaying by internal calibration.

"mol % of diol units" corresponds to the content, in of oxyethylene units "G", di(oxyethylene) units "2G", tri(oxyethylene) units "3G" and tetra(oxyethylene) units "4G", relative to the total amount of diol units.

"% GT/Σ units" corresponds to the mol % of units of formula ($I''^1$)

$$[-CO-A''^1-CO-O-CH_2-CH_2-O-] \qquad (I''^1)$$

where A" is 1,4-phenylene (in Examples 1–7) or naphthalene (in Example 8) relative to the total amount of units of formula ($I'^1$)

$$[-CO-A'^1-CO-O-(CH_2-CH_2O)_n-] \qquad (I'^1)$$

where $A'^1$ is 1,4-phenylene (naphthalene in Example 8), sulpho-1,3-phenylene and optionally 1,3-phenylene and n ranges from 1 to 4.

"% GT/Σ units" is calculated by the following formula:

% GT/Σ units=(mol % of Tp units)×(mol % of G units)/100

The molar mass of the polyesters (Mw) is determined by gel permeation chromatography (GPC) in 100% DMAc/LiBr, the results being given in polystyrene equivalents.

The results presented in Table 1 show that:

if the molar mass is too high, no gelling is observed, even with a high level of "% GT/Σ units" (Comparative Examples 6 and 7)

for a low molar mass, no gelling is observed if the level of "% GT/Σ units" is inadequate (Comparative Example 4)

for a low molar mass, gelling is promoted by a higher level of "% GT/Σ units" (Examples 1, 3 and 5); for a given type of oligomer, the "% GT/Σ units" should be higher the higher the molar mass of the said oligomer (Example 2).

TABLE 1/1

| | Example | | | | | | | |
|---|---|---|---|---|---|---|---|---|
| | 1 | 2 | 3 | 4 | 5 | 6 | 7 | 8 |
| mol % of the diacid units | | | | | | | | |
| Tp or Np | 82 | 82 | 82 | 68 | 68 | 88.4 | 88.4 | 82 |
| Ip | 3 | 3 | 3 | 17 | 17 | 0 | 0 | 3 |
| SIp | 15 | 15 | 15 | 15 | 15 | 11.6 | 11.6 | 15 |
| % GT/Σ units | 46.5 | 43.7 | 54 | 29 | 39 | 47 | 59.7 | 47.6 |
| mol % of the diol units | | | | | | | | |
| G | 56.8 | 53 | 66 | 43.65 | 57.6 | 52.8 | 67.6 | 58 |
| 2G | 30.7 | 32 | 26.5 | 37.3 | 31.3 | 34.2 | 26.4 | 31 |
| 3G | 10 | 12 | 6.5 | 15.1 | 9.2 | 10.7 | 5.2 | 9 |
| 4G | 2.5 | 3 | 1 | 3.95 | 1.9 | 2.3 | 0.8 | 2 |
| Mw | 8000 | 14,000 | 6500 | 8500 | 7800 | 50,000 | 50,000 | 8000 |
| state of the solution 10% aqueous | | | | | | | | |
| at time t = 0 | gel | liquid | gel | liquid | liquid | liquid | liquid | gel |
| at time t = 2 days | gel | liquid/gel* | gel | liquid | liquid/gel* | liquid | liquid | gel |
| state of the solution 20% aqueous | | | | | | | | |
| at time t = 0 | gel | liquid | gel | liquid | liquid | liquid | liquid | gel |
| at time t = 2 days | gel | gel | gel | liquid | gel | liquid | liquid | gel |

*Intermediate between a liquid and a gel

What is claimed is:

1. A process for gelling aqueous media comprising the steps of adding into said media an effective quantity of at least one water-soluble or water-dispersible copolyester oligomer comprising dicarboxylate units of formula (I)

[—CO—A—CO—O—X—O]   (I)

wherein:
A represents an aromatic or aliphatic divalent hydrocarbon group,
X represents a divalent alkylene, cycloalkylene or polyoxyalkylene group, at least 35 mol % of said units of formula (I) being similar units whose corresponding homopolymer is crystalline, and
at least 7 mol % of said units of formula (I) being units in which the group A is a carrier of hydrophilic functional group(s), and
said copolyester oligomer having a weight-average molecular mass less than 20,000.

2. A process for gelling aqueous media according to claim 1, wherein: from 40 to 70 mol % of said units of formula (I) being similar units whose corresponding homopolymer is crystalline, and from 10 to 25 mol % of said units of formula (I) being units in which the group A is a carrier of hydrophilic functional group(s).

3. A process according to claim 1, wherein the groups A are $C_6$–$C_{14}$ mono-arylene groups, $C_6$–$C_{14}$ polyarylene groups, $C_1$–$C_9$ alkylene groups not carrying a hydrophilic functional group, $C_6$–$C_{14}$ monoarylene groups, $C_6$–$C_{14}$ polyarylene groups or $C_1$–$C_9$ alkylene groups carrying hydrophilic functional group(s).

4. A process according to claim 3, wherein the groups A are 1,4-phenylene, 1,3-phenylene, 1,6-naphthalene, 1,6-cyclohexylene, ethylene, trimethylene, tetramethylene, hexamethylene, sulpho-1,4-phenylene, sulpho-1,3-phenylene, sulpho-1,2-phenylene, sulphonaphthalene, sulphobiphenylene or sulphoethylene groups.

5. A process according to claim 1, wherein the groups X are $C_2$–$C_{10}$ alkylene groups or polyoxyalkylene groups of formula (—Y—O)$_y$Y—, Y representing a $C_2$–$C_4$ alkylene group, y ranging from 1 to 5.

6. A process according to claim 1, wherein the chain ends of said copolyester oligomers are similar or different and are of formulae —A—CO—O—(X—O)$_n$—H   (II$_1$)

said groups (II$_1$) being optionally at least partially sulphated or phosphated, —A—CO—O—(X—O)$_{\bar{n}}$—Z   (II$_2$)

—A—CO—Z',   (II$_3$)

or

—A—CO—O—(X'—O)$_{\bar{p}}$—Z''   (II$_4$)

in which formulae
A, X and n have the meaning given above,
Z represents a $C_2$–$C_{31}$ alkyloyl or aryloyl group optionally carrying an anionic functional group,
Z' represents a polyalkoxysulphonate group of formula $(MO_3S)(CH_2)_q(CH_2—CH_2—O)(RO)_r$—, where M is an alkali metal, q is equal to 0 or 1, R is an ethylene or propylene group, r ranges from 0 to 2, and
X' represents a $C_2$–$C_8$ alkylene group, Z'' represents a $C_1$–$C_{30}$ alkyl or aryl group and p ranges from 0 to 6.

7. A process according to claim 6, wherein Z represents a sulphobenzoyl group $MO_3SC_6H_4C(O)—$ where M is an alkali metal.

8. A process according to claim 1, wherein said water-soluble or water-dispersible copolyester oligomers have dicarboxylate repeating units of formula (I), at least 35 mol % of said units of formula (I) being similar units whose group A represents a 1,4-phenylene, 1,3-phenylene, 1,6-naphthalene, 1,6-cyclohexylene, ethylene, trimethylene, tetramethylene or hexamethylene group, and the group X represents a $C_2$–$C_{10}$ alkylene group and whose corresponding homopolymer is crystalline.

9. A process according to claim 1, wherein said water-soluble or water-dispersible copolyester oligomers comprise dicarboxylate units of formula (I')

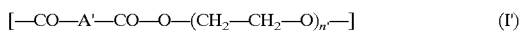
$$[—CO—A'—CO—O—(CH_2—CH_2—O)_{n'}—] \quad (I')$$

in which formula
A' represents a 1,4-phenylene, 1,3-phenylene, 1,6-naphthalene, 1,6-cyclohexylene, ethylene, trimethylene, tetramethylene, hexamethylene or sulpho-1,3-phenylene group n' ranges from 1 to 4, at least 35 mol % of said units of formula (I') being similar units of formula

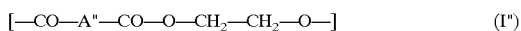
$$[—CO—A''—CO—O—CH_2—CH_2—O—] \quad (I'')$$

where A'' represents a 1,4-phenylene, 1,3-phenylene, 1,6-naphthalene, 1,6-cyclohexylene, ethylene, trimethylene, tetramethylene or hexamethylene group, and at least 7 mol % of said units of formula (I') being units in which the A' group is a sulpho-1,3-phenylene group.

10. A process according to claim 9, wherein the chain ends of said oligomers are similar or different and represented by the groups of formulae

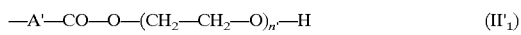
$$—A'—CO—O—(CH_2—CH_2—O)_{n'}—H \quad (II'_1)$$

said groups $(II'_1)$ being optionally at least partially sulphated or phosphated,

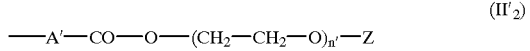
$$—A'—CO—O—(CH_2—CH_2—O)_{n'}—Z \quad (II'_2)$$

$$—A'—CO—Z', \quad (II'_3)$$
or

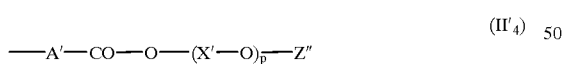
$$—A'—CO—O—(X'—O)_{\overline{p}}—Z'' \quad (II'_4)$$

wherein:
A', X and n' have the meaning given above,

Z represents a $C_2$–$C_{31}$ alkyloyl or aryloyl group optionally carrying an anionic functional group, Z' represents a polyalkoxysulphonate group of formula $(MO_3S)(CH_2)_q(CH_2—CH_2—O)(RO)_r—$, where M is an alkali metal, q is equal to 0 or 1, R is an ethylene or propylene group, r ranges from 0 to 2, and X' represents a $C_2$–$C_8$ alkylene group, Z'' represents a $C_1$–$C_{30}$ alkyl or aryl group and p ranges from 2 to 6.

11. A process according to claim 10, wherein Z represents a $C_2$–$C_{31}$ alkyloyl or aryloyl group optionally carrying a sulphobenzoyl $MO_3SC_6H_4C(O)—$ group where M is an alkali metal.

12. A process according to claim 1, wherein the weight-average molecular mass is from 5000 to 10,000.

13. A process according to claim 9, wherein the water-soluble or water-dispersible copolyester oligomers comprise dicarboxylate units of formula $(I'^1)$

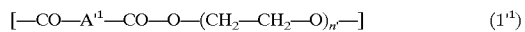
$$[—CO—A'^1—CO—O—(CH_2—CH_2—O)_{n'}—] \quad (I'^1)$$

wherein:
$A'^1$ represents a 1,4-phenylene, sulpho-1,3-phenylene and, optionally, 1,3-phenylene group;

n' ranges from 1 to 4;

at least 35 mol % of said units of formula $(I'^1)$ being similar units of formula

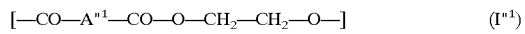
$$[—CO—A''^1—CO—O—CH_2—CH_2—O—] \quad (I''^1)$$

where $A''^1$ represents a 1,4-phenylene group;

at least 7 mol % of said units of formula $(I'^1)$ being units in which the $A'^1$ group is a sulpho-1,3-phenylene group;

optionally up to 20 mol % of said units of formula $(I'^1)$ being units in which the $A'^1$ group is a 1,3-phenylene group; and the weight-average molecular mass of said copolyester oligomers being less than 20,000.

14. A process according to claim 13, wherein the chain ends of said oligomers are similar or different and represented by the groups of formulae

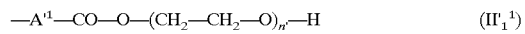
$$—A'^1—CO—O—(CH_2—CH_2—O)_{n'}—H \quad (II'^1_1)$$

said groups $(II'^1_1)$ being optionally at least partially sulphated or phosphated,

$$—A'^1—CO—O—(CH_2—CH_2—O)_{n'}—Z \quad (II'^1_2)$$

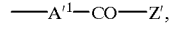
$$—A'^1—CO—Z', \quad (II'^1_3)$$
or

$$—A'^1—CO—O—(X'—O)_{\overline{p}}—Z'' \quad (II'^1_4)$$

wherein:
$A'^1$, X and n' have the definition given above,

Z represents a $C_2$–$C_{31}$ alkyloyl or aryloyl group optionally carrying an anionic functional group, Z' represents a polyalkoxysulphonate group of formula $(MO_3S)(CH_2)_q(CH_2—CH_2—O)(RO)_r—$, where M is an alkali metal, q is equal to 0 or 1, R is an ethylene or propylene group, r ranges from 0 to 2, and X' represents a $C_2$–$C_8$ alkylene group, Z'' represents a $C_1$–$C_{30}$ alkyl or aryl group and p ranges from 0 to 6.

15. A process according to claim 1, wherein said aqueous media consist of water, mixtures of water/solvent(s) compatible with water, simple or multiple "water-in-oil" or "oil-in-water" emulsions present in a plant-protection, pharmaceutical or cosmetic composition.

16. A process according to claim 1, wherein the quantity of copolyester oligomer used represents at least 0.5% by weight of the weight of gelled aqueous medium.

17. A process according to claim 16, wherein the quantity of copolyester oligomer used represents at least about 2% by weight of the weight of the gelled aqueous medium.

* * * * *